United States Patent
Abuzaina et al.

(10) Patent No.: US 8,579,882 B1
(45) Date of Patent: Nov. 12, 2013

(54) CANNULA SYSTEM

(71) Applicant: Covidien LP, Mansfield, MA (US)

(72) Inventors: Ferass Abuzaina, Shelton, CT (US); Ahmad Robert Hadba, Fort Worth, TX (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/914,664

(22) Filed: Jun. 11, 2013

Related U.S. Application Data

(62) Division of application No. 12/147,046, filed on Jun. 26, 2008, now Pat. No. 8,480,651.

(60) Provisional application No. 60/963,049, filed on Aug. 2, 2007.

(51) Int. Cl.
*A61M 25/00* (2006.01)

(52) U.S. Cl.
USPC ............................................. 604/523; 604/518

(58) Field of Classification Search
USPC .................................................. 604/518, 523
See application file for complete search history.

(56) References Cited

U.S. PATENT DOCUMENTS

| | | | |
|---|---|---|---|
| 4,099,528 A | 7/1978 | Sorenson et al. |
| 4,385,631 A | 5/1983 | Uthmann |
| 4,493,696 A | 1/1985 | Uldall |
| 4,610,666 A | 9/1986 | Pizzino |
| 4,737,150 A | 4/1988 | Baeumle et al. |
| 5,053,228 A | 10/1991 | Mori et al. |
| 5,104,375 A | 4/1992 | Wolf et al. |
| 5,126,141 A | 6/1992 | Henry |
| 5,197,951 A | 3/1993 | Mahurkar |
| 5,492,937 A | 2/1996 | Bogentoft et al. |
| 5,525,334 A | 6/1996 | Ito et al. |
| 5,562,653 A | 10/1996 | Thompson |
| 5,575,815 A | 11/1996 | Slepian et al. |
| 5,607,391 A | 3/1997 | Klinger et al. |
| 6,066,325 A | 5/2000 | Wallace et al. |
| 6,132,396 A | 10/2000 | Antanavich et al. |
| 6,149,628 A | 11/2000 | Szapiro et al. |
| 6,152,943 A | 11/2000 | Sawhney |
| 6,290,729 B1 | 9/2001 | Slepian et al. |
| 6,296,831 B1 | 10/2001 | Weller et al. |
| 6,344,488 B1 | 2/2002 | Chenite et al. |
| 6,379,373 B1 | 4/2002 | Sawhney et al. |
| 6,465,001 B1 | 10/2002 | Hubbell et al. |
| 6,562,362 B1 | 5/2003 | Bae et al. |

(Continued)

FOREIGN PATENT DOCUMENTS

| | | |
|---|---|---|
| WO | WO 99/20326 | 4/1999 |
| WO | WO 00/09190 | 2/2000 |

OTHER PUBLICATIONS

Taylor and Francis group; Polymers a property database; 2000, Polymers Profile 1830, Chitosan.

(Continued)

*Primary Examiner* — Kevin C Sirmons
*Assistant Examiner* — Edelmira Bosques

(57) ABSTRACT

The present disclosure provides a cannula useful for introducing a thermally responsive polymer in situ. In embodiments, the cannula possesses more than one cannula, with the thermally responsive polymer introduced in one cannula, and a material such as a coolant in a second cannula which prevents premature gelling of the thermally responsive polymer.

12 Claims, 3 Drawing Sheets

(56) References Cited

U.S. PATENT DOCUMENTS

| | | |
|---|---|---|
| 6,613,021 B2 | 9/2003 | Sogaro |
| 6,626,902 B1 | 9/2003 | Kucharczyk et al. |
| 6,639,014 B2 | 10/2003 | Pathak et al. |
| 6,660,247 B1 | 12/2003 | Gutowska et al. |
| 6,676,971 B2 | 1/2004 | Goupil et al. |
| 6,689,148 B2 | 2/2004 | Sawhney et al. |
| 6,818,018 B1 | 11/2004 | Sawhney |
| 6,923,986 B2 | 8/2005 | Pathak et al. |
| 6,991,804 B2 | 1/2006 | Helmus et al. |
| 7,025,990 B2 | 4/2006 | Sawhney |
| 7,033,571 B2 | 4/2006 | Gutowska et al. |
| 7,070,809 B2 | 7/2006 | Goupil et al. |
| 2002/0193448 A1 | 12/2002 | Wallace et al. |
| 2003/0077242 A1 | 4/2003 | Sawhney |
| 2003/0104032 A1 | 6/2003 | Sawhney et al. |
| 2003/0211073 A1 | 11/2003 | Goupil et al. |
| 2003/0228273 A1 | 12/2003 | Greff |
| 2003/0232746 A1 | 12/2003 | Lamberti et al. |
| 2004/0009205 A1 | 1/2004 | Sawhney |
| 2004/0030282 A1 | 2/2004 | Freyman et al. |
| 2004/0072961 A1 | 4/2004 | Pathak et al. |
| 2004/0096508 A1 | 5/2004 | Gutowska et al. |
| 2004/0228794 A1 | 11/2004 | Weller et al. |
| 2005/0080445 A1 | 4/2005 | Sawhney et al. |
| 2005/0164980 A1 | 7/2005 | Shimoboji |
| 2005/0238722 A1 | 10/2005 | Pathak et al. |
| 2005/0266086 A1 | 12/2005 | Sawhney |
| 2005/0267490 A1 * | 12/2005 | Secrest et al. .................. 606/113 |
| 2006/0013883 A1 | 1/2006 | Nicol et al. |
| 2006/0070631 A1 * | 4/2006 | Scopton et al. ................ 128/898 |
| 2006/0079597 A1 | 4/2006 | Muratoglu et al. |
| 2006/0100370 A1 | 5/2006 | Wellisz et al. |
| 2006/0177481 A1 | 8/2006 | Sawhney |
| 2006/0193899 A1 | 8/2006 | Sawhney |
| 2006/0198865 A1 | 9/2006 | Freyman et al. |
| 2006/0213526 A1 | 9/2006 | McIntyre |
| 2006/0257378 A1 | 11/2006 | Crumpler et al. |
| 2006/0280797 A1 | 12/2006 | Shoichet et al. |
| 2006/0292131 A1 | 12/2006 | Binette et al. |
| 2007/0083155 A1 | 4/2007 | Muller |
| 2007/0243131 A1 | 10/2007 | Chen et al. |

OTHER PUBLICATIONS

Supramolecular Design of Biological Applications; Chapter 3, p. 8; CRC Press LLC 2002.

Encycl. Polym. Sci. Eng. 2nd edn., (eds. H.F. Mark, N.M. Bikales, C.G. Overberger and G. Menges), John Wiley and Sons, 1985, vol. 3. (From Polymers Database).

European Search Report for EP 08252617.9-2310 date of completion is Nov. 10, 2008 (5 pages).

European Search Report for Ep 11005550.6-2320 date of completion is Jul. 24, 2012 (7 pages).

* cited by examiner

CANNULA SYSTEM

CROSS-REFERENCE TO RELATED APPLICATIONS

This application is a divisional of U.S. application Ser. No. 12/147,046 filed Jun. 26, 2008, now patented U.S. Pat. No. 8,480,651, which claims benefit of U.S. Provisional Application Ser. No. 60/963,049 filed Aug. 2, 2007, and the disclosures of each of the above-identified applications are hereby incorporated by reference in their entirety.

TECHNICAL FIELD

The present disclosure relates to cannulas suitable for introducing thermoreversible polymeric materials in situ.

BACKGROUND OF RELATED ART

A polyp is generally a growth that projects from a membrane in the body. The shape of a polyp is often described as pedunculated or sessile. Pedunculated polyps grow on stalks, while sessile polyps may have broad bases and a flat appearance. Often, polyps form on mucous membranes such as those lining the colon, bladder, uterus, cervix, vocal cords, and/or nasal passage and protrude into a body cavity. Polyps are problematic in that they may block a passage, and/or may become cancerous. Generally, the larger the polyp, the more likely it is to become cancerous.

Endoscopic polypectomy procedures are effective in removing pedunculated polyps; however, sessile polyps are often problematic. For example, because of their flat, diffuse appearance, sessile polyps may be difficult to snare and excise with electrocautery. To facilitate excision of some polyps, saline may be injected into the submucosa of a polyp to create an artificial cushion that raises the polyp. However, saline has a short residence time in the submucosa: it usually clears within 4 to 5 minutes after injection.

In addition, large polyps are often difficult to remove as a whole, so they are often excised in piecemeal fashion. After the first excision of polyp tissue, injected solution may escape from the submucosa causing the polyp to collapse, thus making it difficult to remove the remaining portions of the polyp. Although saline may be re-injected, it escapes quickly and is not very effective in raising the remaining portions of the polyp.

Attempts to improve submucosa residence time of injection solutions have been reported. For example, solutions of glycerin, dextrose, hyaluronic acid, and hydroxypropyl cellulose have been reported as injection solutions. In some cases, hyaluronic acid may be effective. The average residence time of hyaluronic acid solutions in porcine esophagus is reportedly 21.5 minutes. However, these solutions may still leak out of the submucosal layer once the cushion is breached during the endoscopic dissection or polypectomy.

Means for introducing injection solutions into a polyp include endoscopic methods which may, in embodiments, include the use of catheters and/or cannulas. As is within the purview of those skilled in the art, cannulas may include tubular, flexible, surgical instruments for withdrawing fluids from (or introducing fluids into) a cavity of the body. Cannulas may have a single lumen or may have multiple lumens; multi-lumen cannulas, including dual lumen cannulas, are also within the purview of those skilled in the art.

Various configurations for multi-lumen catheters and/or cannulas are also known. For example, U.S. Pat. No. 4,385,631 discloses a hemodialysis catheter having two circular lumens arranged side by side. U.S. Pat. No. 4,099,528 discloses a coaxial double lumen cannula and U.S. Pat. No. 4,493,696 describes a coaxial double lumen catheter.

There remains room for improvement in compositions and methods for performing endoscopic polypectomy procedures, as well as instruments suitable for introducing polymeric materials into the body.

SUMMARY

The present disclosure provides multi-lumen cannulas suitable for introducing thermally responsive polymers in situ. Such multi-lumen cannulas may include, in embodiments, a proximal end and a distal end, at least one lumen configured to permit the passage of a coolant, and at least one additional lumen configured to permit the passage of a composition including a thermally responsive polymer, wherein the thermally responsive polymer is in a low viscosity state at a pre-treatment temperature and a higher viscosity state at a treatment temperature that is higher than the pre-treatment temperature.

In embodiments, cannulas of the present disclosure may be utilized to introduce thermally responsive polymers into polyps to aid in their removal.

Methods for applying compositions with these devices are also provided. In embodiments, methods of the present disclosure may include obtaining a composition including a thermally responsive polymer, wherein the composition is in a low viscosity state at a pre-treatment temperature prior to being injected into a polyp and a higher viscosity state at a treatment temperature that is higher than the pre-treatment temperature. The compositions may be administered to the polyp using a multi-lumen cannula including a proximal end and a distal end, at least one lumen configured to permit the passage of a coolant, and at least a second lumen configured to permit the passage of the composition including the thermally responsive polymer. The composition may be warmed thereby increasing the composition's viscosity to the higher viscosity state, and the polyp may be removed while the composition including the thermally responsive polymer remains substantially inside the polyp.

BRIEF DESCRIPTION OF THE DRAWINGS

Various embodiments of the present disclosure will be described herein below with reference to the figures wherein.

DETAILED DESCRIPTION

The present disclosure provides cannulas suitable for introducing compositions containing one or more thermally responsive polymers into the body. In embodiments, the compositions may be in a low viscosity state such as a liquid at a pre-treatment temperature, and a higher viscosity state such as a gel at a treatment temperature that is higher than the pre-treatment temperature.

In accordance with the present disclosure, a multi-lumen cannula may be utilized to introduce the composition containing one or more thermally responsive polymers into the body. The composition containing one or more thermally responsive polymers may be introduced into the body through at least one lumen, with at least one other lumen of the multi-lumen cannula containing a coolant which prevents premature gelling of the thermally responsive polymer as it is introduced into the body or at any injection site.

A multi-lumen cannula for use in accordance with the present disclosure should possess at least two lumens. In embodiments, as noted above, at least one lumen may contain a coolant, with at least one other, lumen possessing the thermally responsive polymer composition. In other embodiments, the cannula may possess additional lumens which may house and permit the transit of other suitable items and/or devices including, but not limited to, one or more medicines, drugs, blood, medical devices, guide wires, snares suitable for use in polypectomy procedures, needles, optical fibers, fiber optic imaging devices, fiber optic diagnostic probes, combinations thereof, and the like.

In embodiments, a suitable multi-lumen cannula may be a double lumen cannula. A double lumen cannula may possess any configuration within the purview of those skilled in the art. For example, in some embodiments, a single tube with a horizontal division of the tube which places the lumens of the cannula in immediate juxtaposition may be utilized.

Figure 1:
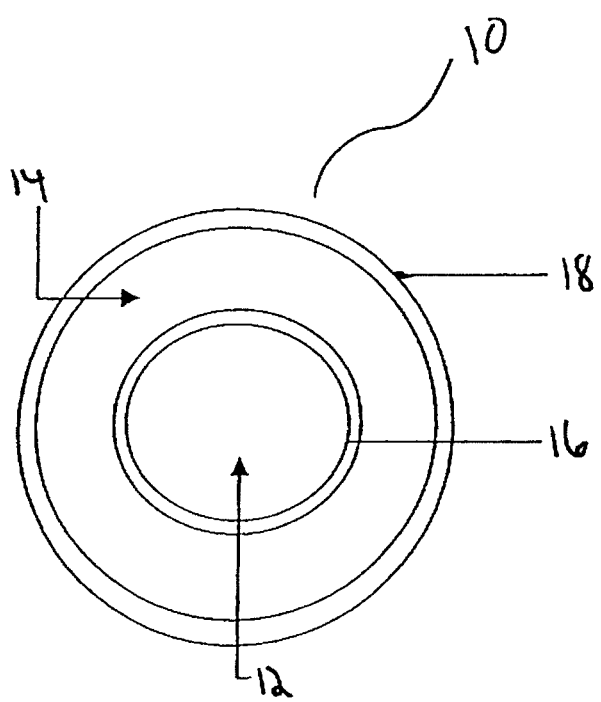
FIG. 1 is a cross section of a cannula of the present disclosure having an inner lumen capable of carrying a thermally responsive polymer and an outer lumen capable of carrying a coolant.

In other embodiments, a coaxial double lumen cannula may be utilized to introduce the composition containing one or more thermally responsive polymers into the body. Such a cannula may possess concentric lumens, disposed one within the other. A cross-section of such a cannula, which should be apparent to one skilled in the art, is depicted in FIG. 1. As depicted in FIG. 1, cannula 10 may include two lumens, inner cannula lumen 12 and outer cannula lumen 14. Inner wall 16 may encompass inner lumen 12, while outer wall 18 may encompass outer lumen 14. The diameter of the inner lumen may be from about 1 mm to about 2 mm, in embodiments from about 1.25 mm to about 1.75 mm. The diameter of cannula 10 may be less than about 2.8 mm, in embodiments from about 2.2 mm to about 2.8 mm.

The composition containing one or more thermally responsive polymers may be introduced into the body via the inner lumen or the outer lumen; the other lumen may contain a coolant to prevent premature gelling of the thermally responsive polymer. For example, the composition containing one or more thermally responsive polymers may be introduced into the body via the outer lumen with the coolant contained in the inner lumen. In other embodiments, the composition containing one or more thermally responsive polymers may be introduced into the body via the inner lumen, with the coolant being present in the outer lumen of the cannula.

A cannula in accordance with the present disclosure may be of any suitable length; in embodiments from about 1 meter to about 2.5 meters long, in other embodiments from about 1.25 meters to about 2.3 meters long.

The cannulas of the present disclosure may be utilized to deliver thermally responsive polymers endoscopically through a conventional colonoscope. Accordingly, while a cannula of the present disclosure may be constructed of any material within the purview of those skilled in the art, in embodiments a cannula of the present disclosure may be constructed of a comparatively soft medical grade plastic or metals such as stainless steel, titanium, and the like. Specific synthetic materials which may be utilized include, but are not limited to, fluoropolymers including polytetrafluoroethylene, polyurethane, polyethylene, polypropylene, high density polyethylene, nylons, polyethylene terephthalate, silicones, combinations thereof, and the like.

Figure 2:
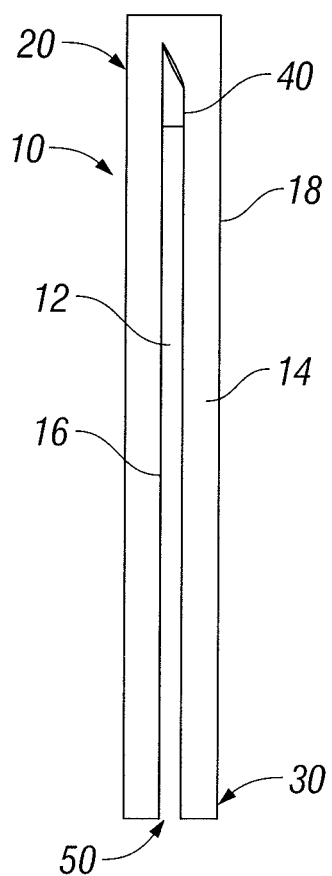
FIG. 2 is a depiction of a cannula of the present disclosure possessing a needle therein.

In embodiments, the inner lumen of the cannula may possess a luer lock fitting at one end and a short dispensing needle at the other end, i.e., the distal end, having a length of from about 3 mm to about 8 mm, in embodiments about 4 mm, with a gauge of from about 14 gauge to about 23 gauge, in embodiments from about 18 gauge to about 21 gauge. An example of such a cannula is depicted in FIG. 2. Cannula 10 may possess outer tube 18 surrounding outer cannula lumen 14, inner tube 16 surrounding inner cannula lumen 12, with needle 40 affixed to the distal end of inner tube 16 adjacent distal end 20 of cannula 10. Outer tube 18 functions as a protective sheath to protect the needle and provide a working channel for any scope utilized therewith (not shown). The outer diameter of outer tube 18 may be of a suitable size, in embodiments less than or equal to about 2.7 mm. The diameter of the inner tube 16 is small enough to permit passage within outer tube 18. The inner diameter of inner tube 16 may be, in embodiments, from about 1 mm to about 2 mm. Needle 40 may, in embodiments, be from about 14 gauge to about 23 gauge, and may be of a length of from about 3 mm to about 8 mm. A thermally responsive polymer may be introduced into inner tube 16 at its proximal end 50 adjacent proximal end 30 of cannula 10 utilizing a luer lock syringe, a mechanically advancing gun, or similar device (not shown).

Figure 3:
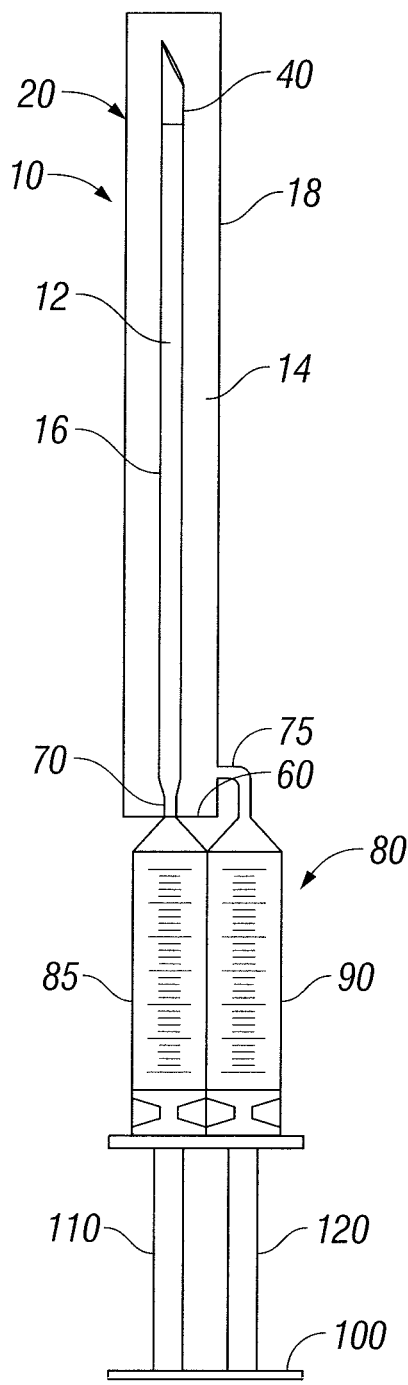
FIG. 3 is another depiction of a cannula of the present disclosure possessing a needle therein with the proximal end of the cannula attached to a double-lumen syringe.

In embodiments, the distal end of the outer lumen of the cannula may be open. Where a coolant is present in the outer lumen of the cannula, a separate port with a luer lock fitting may be utilized to inject the coolant into the outer lumen or the same port may be utilized to simultaneously inject both the thermally responsive polymer and the coolant. Where the same port is utilized to simultaneously inject both the thermally responsive polymer and the coolant, a double-lumen syringe may be utilized with one compartment containing the polymer solution for introduction into the inner lumen and a second compartment containing the coolant for introduction into the outer lumen. An example of such a cannula is depicted in FIG. 3. As set forth in FIG. 3, cannula 10, possessing outer tube 18, inner tube 16, and needle 40 at the distal end of inner tube 16 within distal end 20 of cannula 10, may have a closed proximal end 60 and access ports 70 and 75 which may be connected to a double-lumen syringe 80, possessing lumens 85 and 90. Lumen 85 may possess a thermally responsive polymer which may be introduced via access port 70 into inner cannula lumen 12, while lumen 90 may possess a coolant which may be introduced via access port 75 into outer cannula lumen 14. Double lumen syringe 80 may possess backing 100 on plungers 110 and 120 to facilitate the simultaneous introduction of the thermally responsive polymer and the coolant. In either case, the polymeric material may be introduced into the body via the inner lumen which may, in embodiments, have a needle 40 as described above attached thereto; the coolant may be dispensed out of the distal end of the cannula into the body, for example the colon, where the cannula is utilized to introduce the thermally responsive polymer into a polyp during a polypectomy.

Figure 4:
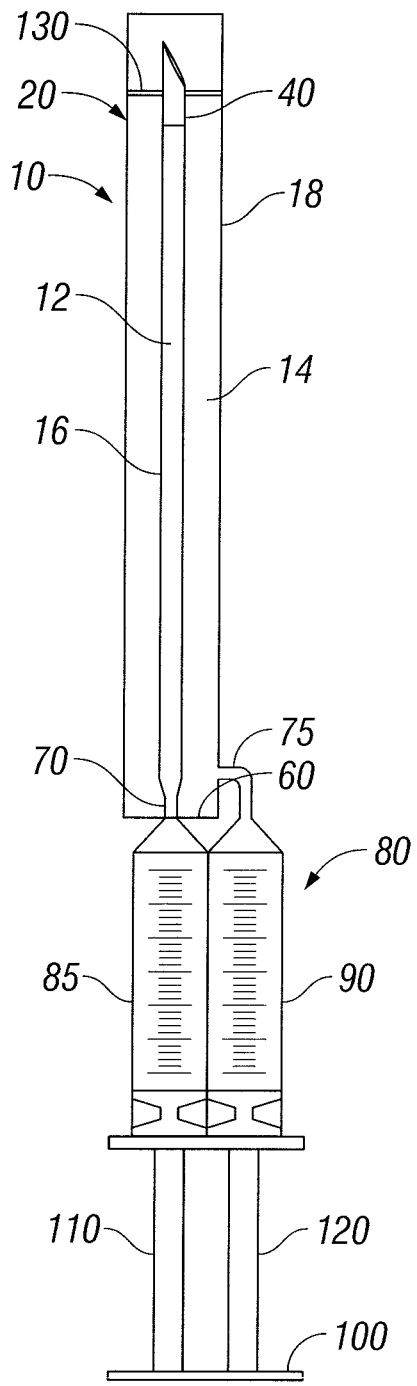
FIG. 4 is another depiction of a cannula of the present disclosure possessing a needle therein, a double-lumen syringe attached to the proximal end of the cannula, and a valve, stopper or seal at the distal end of the cannula.

In yet other embodiments, the distal end of the outer lumen of the cannula may be closed so that the coolant is not discharged into the body. In this embodiment, a valve, stopper, seal, or similar device may be placed at the distal end of the outer lumen which prevents the coolant from exiting the distal end of the cannula. An example of such a cannula is depicted in FIG. 4. As set forth in FIG. 4, cannula 10, possessing outer tube 18, inner tube 16, and needle 40 at the distal end of inner tube 16 within distal end 20 of cannula 10, may have a closed proximal end 60 and access ports 70 and 75 which may be connected to a double-lumen syringe 80, possessing lumens 85 and 90. Lumen 85 may possess a thermally responsive polymer which may be introduced via access port 70 into inner cannula lumen 12, while lumen 90 may possess a coolant which may be introduced via access port 75 into outer cannula lumen 14. Double lumen syringe 80 may possess backing 100 on plungers 110 and 120 to facilitate the simultaneous introduction of the thermally responsive polymer and the coolant. Cannula 10 may possess a stopper, valve, or seal 130 at its distal end 20 which permits passage of needle 40 therethrough but prevents any coolant from exiting outer cannula lumen 14. In embodiments, it may be desirable to determine the volume of the outer lumen and introduce that amount of coolant therein, to minimize backflow of the coolant from the proximal end of the cannula during a surgical procedure.

Any coolant capable of preventing premature gelling of the thermally responsive polymer may be utilized. Suitable coolants which may be included in one of the lumens, in embodiments the outer lumen, include, for example, cooled liquids such as water, saline, ethanol, combinations thereof, and the like, and/or cooled gases such as air, nitrogen, argon, helium, carbon dioxide, combinations thereof, and the like. In some cases, gases may be cooled to a liquid state, for example, liquid nitrogen.

In other embodiments, suitable coolants may include solutions such as ammonium nitrate crystals in water, which are capable of dissolving in water while absorbing heat and cooling their surroundings in a few seconds. Similar solutions which may be utilized as the coolant include, but are not limited to, potassium iodide in water, ammonium chloride in water, ammonium acetate in water, potassium thiocyanate in water, ammonium thiocyanate in water, sodium thiosulfate in water, ammonium bromide in water, combinations thereof, and the like. Other solutions which may be utilized as a coolant include urea based solutions commercially available as INSTAKOOL™ from Nortech Laboratories, Inc. (Farmingdale, N.Y.), and the like. In addition, combinations of chemicals known to produce endothermic reactions, for example, baking soda with citric acid, and the like, may be combined and utilized as a coolant.

Combinations of the above-identified coolants may also be utilized in some embodiments.

In embodiments, the above coolants may be utilized without any external temperature control. In other embodiments, the temperature of the coolant may be adjusted utilizing external means, for example, a suitable control system such as a Peltier cooler, a Joule-Thompson cryostat, a Stirling engine, an independent closed-loop refrigeration system, and the like. Such temperature control systems and their operation are within the purview of those skilled in the art.

Thermally responsive polymers which may be utilized with the cannula of the present disclosure may include one or more polymeric substances that undergo a change in viscosity with a change in temperature, for example, warming. In embodiments, the thermally responsive polymers may be in a solution including at least one solvent, with other excipients and/or ingredients to form a composition of the present disclosure. In embodiments, additional excipients and/or ingredients may be added to facilitate usage of the compositions and adjust their viscosity, for example, during a polypectomy procedure. As used herein, "viscosity" refers to a measure of the resistance of a fluid to deform under shear stress and is used herein to describe a fluid's internal resistance to flow.

For example, water has a relatively lower viscosity, while substances like vegetable oil or honey have a higher viscosity.

Compositions utilized in accordance with the present disclosure may include a pharmaceutically acceptable carrier or diluent, vehicle or medium, for example, a carrier, vehicle or medium that is compatible with the tissues to which they will be applied. The term "dermatologically or pharmaceutically acceptable," as used herein, means that the compositions or constituents thereof are suitable for use in contact with tissues or for use in patients in general without undue toxicity, incompatibility, instability, allergic response, and the like.

The present active ingredients and formulations containing them in accordance with the present disclosure can be injected into the submucosa of a polyp in amounts sufficient to treat the affected area. As used herein the word "treat," "treating" or "treatment" refers to using the active ingredients and/or compositions of the present disclosure prophylactically to prevent outbreaks of any undesirable conditions, or therapeutically to ameliorate an existing undesirable condition. A number of different treatments are now possible, which reduce and/or eliminate undesirable conditions.

As used herein "undesirable condition" refers to any detectable tissue manifestations caused by a polyp or removal thereof. Such manifestations can appear due to a number of factors such as, for example, trauma and/or other diseased or dysfunctional state. Non-limiting examples of such manifestations include the development of bleeding, cancer, inflammation, flakiness and/or other forms of tissue abnormality, and combinations thereof. It is understood, that the listed undesirable conditions are non-limiting and that only a portion of the conditions suitable for treatment in accordance with the present disclosure are listed herein.

Suitable polymers for use as the thermally responsive polymers in accordance with the present disclosure include, but are not limited to, thermoreversible polymers, poloxamers, polyoxyalkylene block copolymers, alkyl cellulose, hydroxyalkyl cellulose, cellulosic ethers, poly(n-isopropylacrylamide), PEG triblock copolymers of L-lactide, glycolide, polyglycolides (PGA), copolymers of glycolides such as glycolide/lactide copolymers (PGA/PLLA) and/or glycolide/trimethylene carbonate copolymers (PGA/TMC), D, L-lactide, L-polylactides (PLA), stereocopolymers of polylactides such as poly-L-lactide (PLLA), poly-DL-lactide copolymers and L-lactide/DL-lactide copolymers, c-caprolactone, trimethylene carbonate (TMC), PEG-grafted chitosan, pectin-chitosan mixtures, methyl cellulose, gelatin, and combinations thereof. Other suitable polymers include glycerin, dextrose, hyaluronic acid, hydroxypropyl cellulose, hydroxyethyl cellulose, hydroxyl propyl methyl cellulose (HPMC), combinations thereof, and the like.

The polymer may be dissolved in a solvent at a concentration of from about 10% to about 70% by weight of the solution, in embodiments from about 20% to about 60% by weight of the solution; thus the solvent may be present in an amount from about 90% to about 30% by weight of the solution, in embodiments from about 80% to about 40% by weight of the solution. In embodiments, the polymer concentration may be such that the composition in accordance with the present disclosure is in a low viscosity state at a pre-treatment temperature and a higher viscosity state at a treatment temperature that is higher than the pre-treatment temperature. The polymer concentration may also be such that the composition in accordance with the present disclosure is in a highly viscous shear thinning state at a pre-treatment temperature and a higher viscosity state at a treatment temperature that is higher than the pre-treatment temperature.

As used herein, "pre-treatment temperature" refers to the temperature of the compositions in accordance with the present disclosure prior to being applied in the body of a patient, for example the submucosa of a polyp. The pre-treatment temperature may be room temperature, for example from about 23° C. to about 25° C., or any temperature below the treatment temperature. As used herein, "treatment temperature" refers generally to the temperature of the compositions in accordance with the present disclosure after being applied to the body, for example the submucosa of a polyp. The treatment temperature may be the normal body temperature for a human, for example about 37° C., or any temperature found within the body, including, for example, the temperature of a polyp to be treated. While the healthy human body can maintain a fairly consistent body temperature of about 37° C., the temperature may vary by about ±2° C., with factors that may affect treatment temperature including the age of the individual, the time of day, or the part of the body in which the temperature is being measured at, and the like.

In embodiments, polyoxyalkylene polymers, including those commercially available under the tradename PLURONICS, may be utilized as the thermally responsive polymer. These polymers are commercially available from BASF Corporation. Such polymers are closely related block copolymers classified as polyoxypropylene-polyoxyethylene condensates that terminate in primary hydroxyl groups, and may be formed by the condensation of propylene oxide into a propylene glycol nucleus followed by the condensation of ethylene oxide onto both ends of the polyoxypropylene base. The polyoxyethylene hydrophilic groups on the ends of the base pre-polymer may be controlled in length so that they account for from about 10% to about 80% by weight of the final polymer. The PLURONIC polymer series of products may be represented empirically by the formula: $HO(C_2H_4O)_a (C_3H_6O)_b (C_2H_4O)_c H$, where a and c are statistically equal.

The thermally responsive polymer may include a mixture of other polyoxyalkylene polymers and/or various PLURONIC polymers. In some embodiments, a first block copolymer and a second block copolymer may be utilized. For example, a first block copolymer of ethylene oxide and propylene oxide, such as PLURONIC F-127, may be mixed with a second block copolymer of ethylene oxide and propylene oxide, such as PLURONIC F-68, in a solution. In some embodiments, the first block copolymer may be present in amounts of from about 10% to about 50% by weight of the solution. The first block copolymer such as PLURONIC F-127 may have a solubility in water at about 4° C. of greater than about 10%. (As concentration increases, the gelation temperature decreases.) In other embodiments, the first block copolymer may be present in amounts of from about 15% to about 30% by weight of the solution.

The second block copolymer, in embodiments F-68, may be present in an amount of from about 5% to about 50% by weight of the solution. The second block copolymer, such as, for example, PLURONIC F-68, may have a solubility in water at about 4° C. of greater than about 10%. In embodiments, the second block copolymer may be present in an amount of from about 5% to about 25% by weight of the solution.

The first block copolymer, the second block copolymer, or both, may have a molecular weight of from about 7680 to about 14600. In embodiments, the first block copolymer may have a molecular weight of from about 7680 to about 9510, while the second block copolymer may have a molecular weight of from about 9840 to about 14600.

In some embodiments, suitable compositions of the present disclosure may include a solvent, from about 10% to about 50% by weight of a first block copolymer of ethylene oxide and propylene oxide, and from about 5% to about 50% by weight of a second block copolymer of ethylene oxide and propylene oxide. In other embodiments, suitable compositions may include an aqueous solvent, and about 15% to about 50% by weight of a thermally responsive polymer admixture.

In embodiments, the first and second block copolymers may be thermoreversible. Suitable thermoreversible polymers may be added to the compositions in accordance with the present disclosure in an amount sufficient to reversibly change the viscosity thereof in response to changes in temperature. For example, a composition having a high viscosity at 37° C. may thin and have a low viscosity at 25° C., yet thicken again upon application of heat. Thus, such a composition may be a liquid at about 25° C. and a gel at a treatment temperature of about 37° C.

In embodiments, thermoreversible polymers may be added to an aqueous solution incorporating a stable combination or admixture of one or more thermoreversible polymers and/or thermally responsive polymers in amounts sufficient to effectively produce reversible gelation at predetermined temperatures. As used herein, reversible gelation refers to the increase and/or decrease in the viscosity of a composition due to a variation in temperature, where the composition becomes a gel or gel-like at one temperature, and a liquid at another lower temperature. Non-limiting examples of suitable thermoreversible polymers for use herein include alkyl celluloses, hydroxyalkyl celluloses, cellulosic ethers, PLURONIC® polymers and TETRONIC® polymers, and combinations thereof. In embodiments, thermoreversible polymers may be added in an amount of from about 10% to about 50% by weight of the composition of the present disclosure.

In embodiments, compositions for use with a cannula in accordance with the present disclosure may include hyaluronic acid and/or derivatives thereof, such as sodium hyaluronic acid. In other embodiments, the compositions in accordance with the present disclosure may be devoid of hyaluronic acid and/or derivatives thereof such as sodium hyaluronic acid, or hyaluronic acid or derivatives thereof combined with any other chemical.

In embodiments, compositions in accordance with the present disclosure may transition from a liquid state to a gel or gel-like state at a temperature of from about 5° C. to about 40° C., in embodiments at a temperature of from about 15° C. to about 37° C., and in other embodiments at a temperature of from about 25° C. to about 35° C. In embodiments, the transition temperature can be modified by including polymers such as PLURONIC F-68 in the composition.

Additionally, additives may be utilized to adjust the temperature at which the compositions of the present disclosure form a semi-solid, sometimes referred to herein as a gel. Any additive within the purview of those skilled in the art may be utilized. The additives may be hydrophilic or hydrophobic. In embodiments, suitable hydrophilic additives include polyalkylene oxides such as polyethylene glycols (PEG) of varying molecular weights such as PEG 8000, PEG 10000 and the like, n-sodium octyl sulfate, n-sodium decyl sulfate, n-dodecyl sulfate, n-hexadecyl sulfate, n-octadecyl sulfate, combinations thereof, and the like. Suitable other additives include, but are not limited to, salts such as NaCl, $Na_2SO_4$, $CaCl_2$, dyes such as methylene blue and isosulfan blue, antifoam agents, bioactive agents, combinations thereof, and the like. For example, in some embodiments SURFYNOL® MD-20, a non-silicone solvent-free liquid defoamer from Air Products and Chemicals, Inc. (Allentown, Pa.), may be added to adjust the gel temperature of a composition of the present disclosure.

In yet other embodiments, surfactants may be added to compositions of the present disclosure to adjust the gel temperature. Suitable surfactants are within the purview of those skilled in the art and include, for example, sorbitan esters, polyolefin based surfactants, ethoxylates, combinations thereof, and the like. In some embodiments, commercially available surfactants such as TRITON® 100 and TRITON® 114 (nonionic surfactants from Sigma-Aldrich); TWEEN surfactants, SPAN surfactants, combinations thereof, and the like, may be utilized. Suitable TWEEN and SPAN surfactants include, but are not limited to, monolaureates (TWEEN 20, TWEEN 21, SPAN 20), monopalmitates (TWEEN 40, SPAN 40), monostearates (TWEEN 60, TWEEN 61, SPAN 60), tristearates (TWEEN 65, SPAN 65), monooleates (TWEEN 80, TWEEN 81, SPAN 80), trioleates (TWEEN 85, SPAN 85), combinations thereof, and the like.

Where utilized, the amount of such additives utilized to adjust the gel temperature of a composition of the present disclosure may vary from about 0.01% by weight to about 4% by weight of the composition, in embodiments from about 0.1% by weight to about 2.5% by weight of the composition, in embodiments from about 1% by weight to about 2.25% by weight of the composition, in other embodiments from about 1.5% by weight to about 2% by weight of the composition.

By adjusting the concentration of the copolymers and any additives, liquid to semi-solid transition temperatures between a pre-treatment temperature and a treatment temperature can be achieved. For example, the concentration of the thermally responsive polymers and the use of additives can be adjusted to provide compositions in accordance with the present disclosure that are a liquid at a pre-treatment temperature, and a gel at treatment temperature. In embodiments, the liquid-gel transition temperature may be from about 5° C. to about 65° C. In some embodiments, the constituents can be selected in predetermined amounts to produce high viscosity, shear thinning, gel compositions. Such high viscosity, shear thinning, compositions may be suitable for injection in a high viscosity state such as a gel. In embodiments, the compositions in accordance with the present disclosure at 25° C. have a viscosity of from about 50 centipoise to about 200,000 centipoise.

In shear thinning embodiments, compositions in accordance with the present disclosure transition from a semi solid and/or gel state to a more viscous semi-solid and/or gel state at a temperature from about 5° C. to about 50° C., in embodiments at a temperature from about 15° C. to about 40° C., and in some embodiments at a temperature from about 30° C. to about 37° C. As compositions of the present disclosure may be used in the human body, in embodiments it may be desirable for the composition of the present disclosure to gel at a temperature close to human body temperature, which is about 37° C.

In other embodiments, a solvent utilized to form compositions for use in accordance with the present disclosure may be water, saline, or any pharmaceutically acceptable solvent in amounts sufficient to solubilize the ingredients of the composition. For example, a non-limiting example of a suitable solvent includes an aqueous solution such as saline, resuspension buffer such as a phosphate buffered saline, or a buffer suitable for injection into a patient. Non-limiting examples of solvents and/or buffers suitable for injection into a patient include a pharmaceutically acceptable carrier such as a solution that does not cause allergic or other adverse reaction with the patient upon injection. The solvent may be present in an amount of from about 30% to about 90% by weight of the total composition. In embodiments, the concentration of water in the composition can be from about 30% to about 90% by weight of the composition, and/or from about 40% to about 80% by weight of the composition. The water used in forming the aqueous solution may be purified, as by distillation, filtration, ion-exchange, and the like.

Other excipients can be added to the compositions of the present disclosure in amounts sufficient to promote the removal of one or more polyps. For example, a dye may be added to the compositions to help the surgeon see the polyp better during the removal process. Non-limiting examples of suitable dyes include methylene blue, isosulfan blue, and combinations thereof. Dyes may be added in an amount of about 0.1% to about 2% by weight of the total composition.

Active ingredients can be added to the compositions of the present disclosure in amounts sufficient to benefit the patient and the procedure for which the composition is provided, in embodiments a polypectomy procedure. While the amount of active agent used will depend on a number of factors including the specific active agent chosen and the benefit to be achieved, generally, an amount of from about 0.01% to about 10% by weight of the total composition may be suitable. Non-limiting examples of suitable active ingredients include enzymes such as thrombin that converts fibrinogen to fibrin, vasoconstrictors such as epinephrine, norepinephrine, angiotensin, or vasopressin, chemotherapeutic agents such as fluorouracil (5-FU), antimicrobials, antibiotics, and combinations of these active agents.

In embodiments, compositions and product forms for use in accordance with the present disclosure contain one or more active ingredients in an effective amount to improve undesirable conditions. As used herein "effective amount" refers to an amount of a compound or composition having active ingredients such as enzymes such as thrombin, vasoconstrictors such as epinephrine, norepinephrine, angiotensin, or vasopressin, chemotherapeutic agents such as fluorouracil (5-FU), and combinations of these active agents in amounts sufficient to induce a particular positive benefit to the polyp or tissue adjacent thereto. The positive benefit can be health-related. In embodiments, the positive benefit may be achieved by contacting tissue with a coagulation protein to promote clotting and closure of the excised tissue. In embodiments, the positive benefit may be achieved by contacting tissue with a vasoconstrictor to reduce bleeding. In embodiments, the positive benefit is achieved by contacting tissue with a chemotherapeutic agent to kill cancerous cells.

The pH of the compositions can be adjusted to from about 4 to about 8. Agents suitable for adjusting the pH of the compositions include, but are not limited to, buffering salts such as $NaH_2PO_4$, $NaHPO_4$, $KH_2PO_4$, $K_2HPO_4$, $NaHCO_3$, and $Na_2CO_3$, as well as mineral acids and bases such as hydrochloric acid and sodium hydroxide. The pH adjustment agents may be present in an amount of from about 0.01 to about 5% by weight of the total composition. In embodiments, the pH adjustment agent may be present in an amount of from about 0.1 to about 1% by weight of the total composition.

In embodiments, the cannulas of the present disclosure may be utilized to introduce a composition for use in endoscopic polypectomy. Where utilized in a polypectomy procedure, compositions may be applied to the submucosa of one or more polyps to improve presentation of the polyp and make the polyp easier to capture with an endoscopic instrument such as a snare. For example, compositions having one or more thermoreversible and/or thermally responsive polymers may be injected into the submucosa of a polyp to improve its presentation.

The use of a thermally responsive polymer in compositions of the present disclosure provides the ability to deliver or inject a liquid, gel-on-contact material to the submucosa of one or more polyps to promote removal thereof. As used herein, a gel refers to a semisolid or semi-rigid system including a network of solid aggregates in which liquid is held. By using a liquid delivery, it is possible to quickly and efficiently treat a polyp with gelation upon delivery to the warm tissues. By introducing such materials by way of a multi-lumen cannula possessing a coolant in one cannula, premature gelling of these polymers may be avoided.

In embodiments, compositions in accordance with the present disclosure may be shear thinning and show a decrease in viscosity with increasing rate of shear. Such shear thinning embodiments may be suitable for injection into the submucosa of one or more polyps in a highly viscosity state such as a gel at pre-treatment temperatures. The application of highly viscous shear thinning compositions in accordance with the present disclosure provide the benefit of reducing and/or eliminating time needed for low viscosity compositions to become highly viscous upon warming. In embodiments, highly viscous shear thinning compositions at the pretreatment temperature may become even more viscous at the treatment temperature. In embodiments, use of a shear thinning composition may reduce and/or eliminate a warming step needed to thicken the compositions.

Polyps requiring removal may be pre-treated with one or more compositions in accordance with the present disclosure which include solvents and one or more polymers such as thermoreversible polymers and/or thermally responsive viscosity modifiers. These compositions may be in a low viscosity state at a pre-treatment temperature and a higher viscosity or gel state at a treatment temperature that is higher than the pre-treatment temperature. In some embodiments additives may be included in the compositions of the present disclosure to further adjust the temperature at which the composition forms a gel.

Preconditioning polyps by injecting the compositions in accordance with the present disclosure into the submucosa of one or more polyps may enhance the benefits of polypectomy, for example, by raising the polyps with a composition that gels or becomes more viscous when heated or applied to a patient's warm body, and/or does not readily escape polyps after initial incision thereof. Such preconditioning further improves the presentation of a polyp making it easier to grab and/or snare during excision.

In addition, treatment regimens in accordance with the present disclosure may improve a passage blocked by one or more polyps, and/or facilitate the removal of tissue having a propensity to develop into a cancerous lesion. Compositions in accordance with the present disclosure, at a pretreatment temperature and in a low viscosity state prior to being injected, may be injected into the submucosa of one or more polyps and allowed to warm to the treatment temperature such that the compositions increase in viscosity to a higher viscosity state such as a gel. In embodiments, the viscosity of the compositions in accordance with the present disclosure at the treatment temperature may be higher then the viscosity of the compositions at the pre-treatment temperature. Treatment may then continue by removing the one or more polyps while the more viscous compositions in accordance with the present disclosure remain substantially in the submucosa and to some extent in the polyp.

The various constituents of the compositions in accordance with the present disclosure may be combined with numerous ingredients to form products to be applied to the polyp, or other tissues of humans or other mammals.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A method of applying a composition comprising:
   obtaining a composition comprising a thermally responsive polymer, wherein the composition is in a low viscosity state at a pre-treatment temperature prior to being injected into a polyp and a higher viscosity state at a treatment temperature that is higher than the pre-treatment temperature;
   administering the composition to the polyp using a multi-lumen cannula comprising:
   a proximal end and a distal end;
   at least one lumen configured to permit the passage of a coolant; and
   at least a second lumen configured to permit the passage of the composition comprising the thermally responsive polymer;
   warming the composition thereby increasing the composition's viscosity to the higher viscosity state, and
   removing the polyp while the composition comprising the thermally responsive polymer remains substantially inside the polyp.

2. The method of claim 1, wherein the cannula comprises a coaxial double lumen cannula comprising an inner lumen possessing the composition comprising the thermally responsive polymer and an outer lumen possessing the coolant.

3. The method of claim 2, wherein the distal end of the outer lumen of the cannula possesses a device selected from the group consisting of valves, stoppers and seals, to prevent the coolant from exiting the distal end of the cannula.

4. The method of claim 2, wherein the distal end of the inner lumen of the cannula possesses a dispensing needle.

5. The method of claim 1, wherein the coolant is selected from the group consisting of water, saline, air, nitrogen, argon, helium, carbon dioxide, ethanol, and combinations thereof.

6. The method of claim 1, wherein the coolant comprises a solution selected from the group consisting of ammonium nitrate crystals in water, potassium iodide in water, ammonium chloride in water, ammonium acetate in water, potassium thiocyanate in water, ammonium thiocyanate in water, sodium thiosulfate in water, ammonium bromide in water, urea based solutions, and combinations thereof.

7. The method of claim 1, wherein the composition comprising the thermally responsive polymer is selected from the group consisting of alkyl cellulose, hydroxyalkyl cellulose, cellulosic ethers, poloxamers, polyoxyalkylene block copolymers, poly(n-isopropylacrylamide), PEG triblock copolymers of L-lactide, glycolide, polyglycolide, copolymers of glycolide, glycolide/lactide copolymers, glycolide/trimethylene carbonate copolymers, D, L-lactide, L-polylactides, poly-L-lactide, poly-DL-lactide copolymers, L-lactide/DL-lactide copolymers, .epsilon.-caprolactone, trimethylene carbonate, PEG-grafted chitosan, pectin-chitosan mixtures, methyl cellulose, gelatin, thermoreversible polymers, and combinations thereof.

8. The method of claim 1, wherein the composition comprising the thermally responsive polymer comprises a solvent and from about 10% to about 50% by weight of one or more thermally responsive viscosity modifiers comprising a mixture of a first block copolymer of ethylene oxide and propylene oxide and a second block copolymer of ethylene oxide and propylene oxide.

9. The method of claim 8, wherein the composition comprising the thermally responsive polymer comprises a first block copolymer having an average molecular weight of from about 7680 to about 14600 present in an amount of about 10% to about 50% by weight of the total composition, in combination with a second block copolymer having an average molecular weight of from about 7680 to about 14600 present in an amount of from about 5% to about 50% by weight of the total composition.

10. The method of claim 1, wherein the composition comprising the thermally responsive polymer further comprises one or more active ingredients selected from the group consisting of enzymes, vasoconstrictors, chemotherapeutic agents, antimicrobials, antibiotics, and combinations thereof.

11. The method of claim 1, wherein the composition comprising the thermally responsive polymer has a viscosity of from about 50 centipoise to about 200,000 centipoise at about 25° C.

12. The method of claim 1, wherein the composition comprising the thermally responsive polymer is a liquid at a pre-treatment temperature of about 25° C. and a gel at a treatment temperature of about 37° C.

* * * * *